US00PP28551P3

(12) United States Plant Patent
Olesen

(10) Patent No.: US PP28,551 P3
(45) Date of Patent: Oct. 24, 2017

(54) ***CLEMATIS* PLANT NAMED 'EVIPO068'**

(50) Latin Name: *Clematis viticella*
Varietal Denomination: Evipo068

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 48 days.

(21) Appl. No.: 14/756,241

(22) Filed: Aug. 20, 2015

(65) Prior Publication Data

US 2017/0055410 P1 Feb. 23, 2017

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

Poulsen Roser A/S, Perfection by Poulsen, Jan. 2013.*

* cited by examiner

*Primary Examiner* — Keith Robinson

(57) ABSTRACT

A new *Clematis* plant with a compact growth habit, profuse, red-purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

1 Drawing Sheet

Botanical classification:
Genus: *Clematis.*
Species: *viticella.*
Variety denomination: 'Evipo068'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2001 and the resulting seeds were planted the following winter in a controlled environment in Guernsey, Channel Islands, United Kingdom. The new variety named 'Evipo068' originated as a single seedling from the stated cross.

The new *clematis* plant may be distinguished from its female seed parent and male pollen parent by the following characteristics. The female seed parent is less compact than the new variety. The male pollen parent has red flowers, while the new variety has red-purple flowers.

The objective of the hybridization of this *clematis* plant was to create a new and distinct variety for nursery culture with unique qualities such as:

1. Uniform and abundant red-purple flowers;
2. Vigorous and compact growth, making the variety suitable for container culture:
3. Improved disease resistance; and
4. Non climbing habit.

This combination of qualities was lacking in *clematis* plants that were in commercial cultivation and the qualities have been substantially achieved in the new variety.

'Evipo068' was selected by Mogens N. Olesen and Raymond J. Evison in their *clematis* development program in the Channel Islands, United Kingdom in 2003. Asexual reproduction of 'Evipo068' by means of vegetative stem cuttings and traditional layering was first performed by Mogens N. Olesen and Raymond J. Evison in the nursery during the summer of 2003. This initial and subsequent asexual propagations have demonstrated that the characteristics of 'Evipo068' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo068'. Specifically illustrated in the drawing are flowers at various stages of development, flower in parts, leaves, and a stem exhibiting a cluster of flower buds. Plants shown are 2 years of age.

DETAILED DESCRIPTION OF THE VARIETY:

The following is a detailed description of 'Evipo068', as observed in its growth throughout the flowering period in Yamhill County Oreg. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo016' described and illustrated in U.S. Plant Pat. No. 21,583 are compared to 'Evipo068' in Chart 1.

CHART 1

| | 'Evipo068' | 'Evipo016' |
|---|---|---|
| Flower diameter | 80 to 100 mm | 130-185 mm |
| Tepal upper surface | Red-Purple Group 71A | Red 53 A |
| Tepal count | 6 | normally 6 |

FLOWER AND FLOWER BUD

Blooming habit: Continuous. The natural flowering period is generally from May to September.

Flower bud:

*Size*.—Normally 25 mm in length. Bud diameter is 10 mm.

*Bud form*.—Broad based elliptic.

*Bud color*.—At ¼ opening Yellow-Green Group 144B with strong intonations of Greyed-Purple Group 187A.

Peduncle:

*Surface texture*.—Pubescent.

*Length*.—On average 25 mm.

*Color*.—Yellow-Green Group 144A.

*Strength*.—Moderately strong.

Receptacle:

*Surface texture*.—Pubescent.

*Shape*.—Broad funnel.

*Size*.—2 mm (h)×4 mm (w).

*Color*.—Yellow-Green Group 144A.

Flower arrangement:

*Location on vine*.—New and old growth.

*Borne*.—Normally 5 to 7 flowers per flowering stem.

*Attitude on vine*.—Upward and outward.

Flower bloom:

*Size*.—On average, flowers are 80 to 100 mm in diameter and 20 mm in depth.

*Profile*.—Open flowers are slightly cupped.

*Fragrance*.—None.

*Lasting quality*.—Flowers normally remain up to 10 days on the plant.

Tepals:

*Tepal color*.—The upper surface is Red-Purple Group 71A. The lower surface is Purple Group N77B with a central bar of Purple Group 76B.

*Quantity*.—Normally 6 tepals.

*Size*.—45 mm in length by 26 mm wide.

*Shape*.—Individual tepal shape is ovate. The tepal apex is acuminate. The tepal base is typically acute.

*Arrangement*.—Overlapping.

*Apex recurvature*.—Flat.

*Tepal cross section*.—Slightly reflexed to flat.

*Margins*.—Entire. Strong undulations of margin observed.

*Persistence*.—Tepals drop off cleanly.

Reproductive organs:

*Arrangement*.—Open.

*Pollen*.—None observed.

*Filaments*.—Size: 6 mm in length. Color: Red-Purple Group 70A.

*Anthers*.—Color: Greyed-Purple Group N186A. Length: 4 mm. Quantity: On average, 70.

*Pistils*.—Quantity: On average, 15.

*Stigmas*.—Inferior in location relative to the length of the filaments and the height of the anthers.

*Styles*.—Color: Green White Group 157A. Length: 11 mm.

Seed head characteristics:

PLANT

Plant form: Creeping.

Plant growth: Very compact.

Size: Seasons growth attains 25 cm in height. Average spread is 50 cm.

Stems:

*Color*.—Juvenile stems are Yellow-Green Group 144B. Mature stems are Greyed-Purple Group 187A.

*Internodes*.—On average, 6 cm between nodes.

*Length*.—Normally 20 cm from the base of the plant to the flowering portion of the stem.

*Diameter*.—Normally 3 mm.

*Texture*.—Mature stems are ribbed.

Plant foliage:

*Leaf characteristics*.—Deciduous.

*Arrangement*.—Three to five leaflets.

*Leaf size*.—Compound leaves are normally 145 mm (l)×150 mm (w). Leaflets are normally 65 mm (l)×25 mm (w).

*Abundance*.—On average 1 leaf per 10 cm of stem.

*Leaf color*.—Juvenile upper Yellow-Green Group 144A. Juvenile lower Yellow-Green Group 144A. Mature upper Yellow-Green Group 147A. Mature lower Yellow-Green Group 147B.

*Stipules*.—Absent.

*Petioles*.—Size: Normally 45 mm in length by 1 mm diameter. Texture: Smooth. Color: Greyed-Purple Group 187A.

*Petioloule*.—Size: Normally 35 mm in length by 1 mm diameter. Texture: Smooth. Color: Greyed-Purple Group 187A.

*Leaflet shape*.—Generally elliptic. The base is obtuse. The apex is acute.

*Margin*.—Entire.

*Surface*.—The upper and lower surfaces are smooth.

*Thickness*.—Average.

*Glossiness*.—Moderately Glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

I claim:

1. A new and distinct variety of *clematis* plant named 'Evipo068', substantially as described and illustrated, due to its abundant red-purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

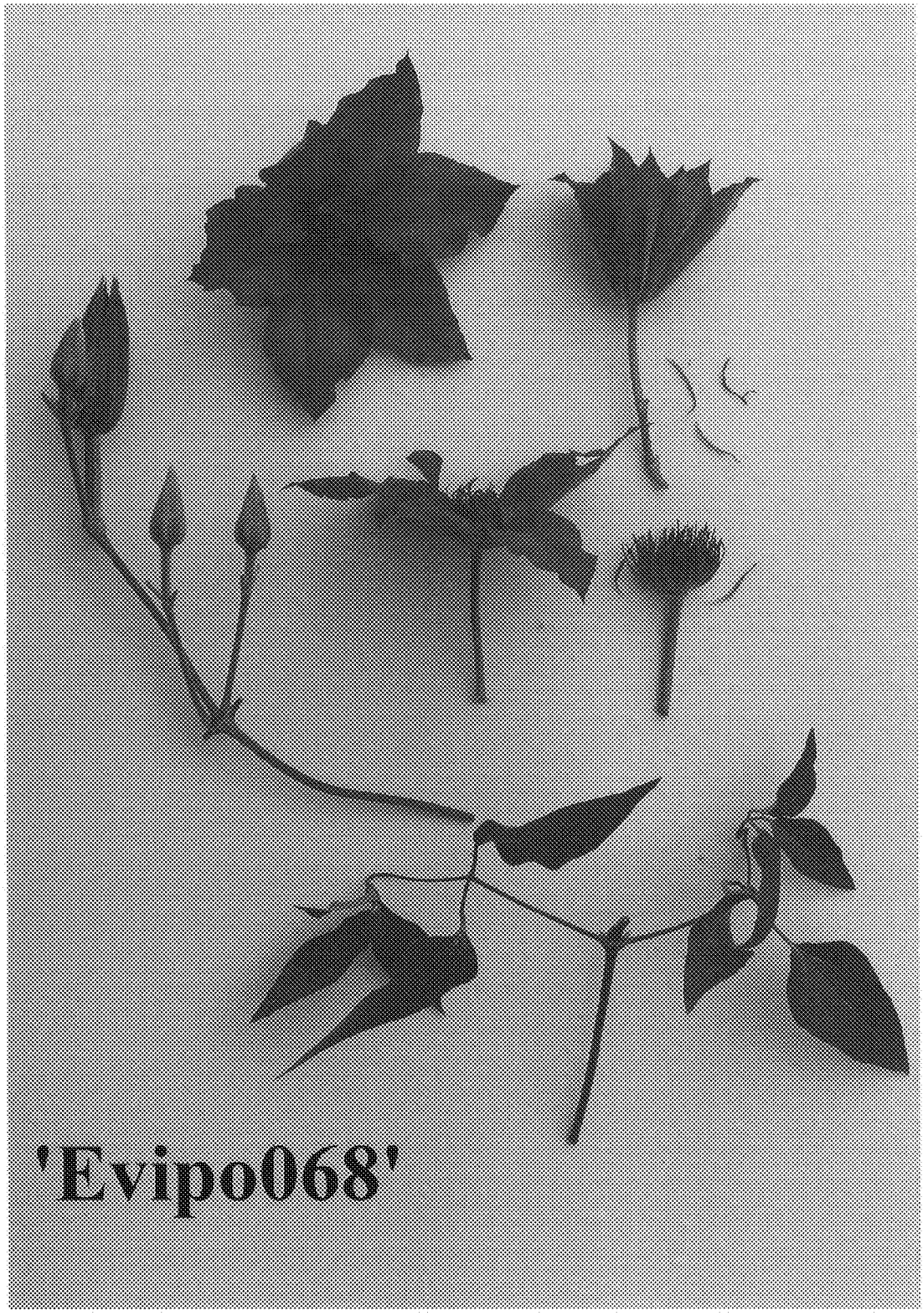
'Evipo068'